(12) United States Patent
Saxena et al.

(10) Patent No.: US 7,507,981 B2
(45) Date of Patent: Mar. 24, 2009

(54) SYSTEM FOR IDENTIFYING A CHARACTERISTIC OF A PRINTING MEDIA

(75) Inventors: Kuldeep Kumar Saxena, Singapore (SG); Wee Sin Tan, Singapore (SG); Deng Peng Chen, Singapore (SG)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 108 days.

(21) Appl. No.: 11/443,411

(22) Filed: May 30, 2006

(65) Prior Publication Data

US 2007/0278432 A1  Dec. 6, 2007

(51) Int. Cl.
*G01N 21/86* (2006.01)

(52) U.S. Cl. .................. 250/559.4; 250/559.16; 250/559.18; 347/19

(58) Field of Classification Search ............ 250/559.16, 250/559.18, 559.4; 356/445, 446, 448; 347/19; 399/45
See application file for complete search history.

(56) References Cited

U.S. PATENT DOCUMENTS

| | | | |
|---|---|---|---|
| 3,636,361 A * | 1/1972 | Bowers | 250/349 |
| 4,414,476 A * | 11/1983 | Maddox et al. | 250/559.37 |
| 5,139,339 A * | 8/1992 | Courtney et al. | 356/446 |
| 5,162,660 A * | 11/1992 | Popil | 250/559.01 |
| 5,856,833 A * | 1/1999 | Elgee et al. | 347/19 |
| 5,925,889 A * | 7/1999 | Guillory et al. | 250/559.16 |
| 6,246,859 B1 * | 6/2001 | Takemura et al. | 399/371 |
| 6,325,505 B1 * | 12/2001 | Walker | 347/105 |
| 6,386,669 B1 * | 5/2002 | Scofield et al. | 347/14 |
| 6,419,342 B1 * | 7/2002 | Bronswijk et al. | 347/19 |
| 6,485,124 B1 * | 11/2002 | King et al. | 347/19 |
| 2003/0081038 A1 | 5/2003 | Valero | |
| 2004/0251435 A1 | 12/2004 | Sawayama et al. | |
| 2005/0068773 A1 * | 3/2005 | Ng et al. | 362/253 |

FOREIGN PATENT DOCUMENTS

JP  11067976 A * 3/1999

* cited by examiner

*Primary Examiner*—Stephen Yam

(57) ABSTRACT

A system for identifying a characteristic of a printing media includes a light source module that has a light emitting diode (LED) and an aspheric lens and a light detection module that has a photodetector and an aspheric lens. The light source module and light detection module are oriented with respect to a printing media such that the focusing points of the respective aspheric lenses are located at a common position on the printing media. The system differentiates between printing media types by applying light to the surface of the printing media and measuring the light that is reflected from the surface.

19 Claims, 6 Drawing Sheets

SYSTEM FOR IDENTIFYING A CHARACTERISTIC OF A PRINTING MEDIA

BACKGROUND OF THE INVENTION

In some printers, the printing technique applied to each print job can be customized to correspond to the type of paper that is to be used. For example, the printing technique applied to plain paper may be different from the printing technique applied to glossy paper. While it is possible for a user to designate the type of paper that is to be used for each print job, this approach is subject to user error. For example, the user may change the paper type in the printer but forget to select the corresponding paper type in the printer interface or the user may select a desired paper type in the printer interface but forget to change the paper in the printer to the desired type. To ensure that the printing technique applied to each print job matches the paper type, it is desirable to be able to automatically determine the type of printing media in the printer. A technique for determining the type of printing media should be compatible with the small geometries of many printers and should provide reliable results.

SUMMARY OF THE INVENTION

A system for identifying a characteristic of a printing media includes a light source module that has a light emitting diode (LED) and an aspheric lens and a light detection module that has a photodetector and an aspheric lens. The light source module and light detection module are oriented with respect to a printing media such that the focusing points of the respective aspheric lenses are located at a common position on the printing media. The system differentiates between printing media types by applying light to the surface of the printing media and measuring the light that is reflected from the surface. Printing media with a smooth surface, such as glossy photo-quality printing paper, tends to reflect a majority of light at the angle of incidence of the light. In contrast, printing media with a rougher surface, such as plain paper, tends to diffuse light over a wide area. By strategically positioning the light source and light detection modules, it is possible to characterize the printing media type based on the detected light. Using light modules with aspheric lenses, the system can be configured to fit small geometries for printer applications and can generate output signals at at least a 1:5 ratio in response to plain paper and glossy paper. A 1:5 response ratio enables the system to reliably distinguish between plain and glossy paper.

Other aspects and advantages of the present invention will become apparent from the following detailed description, taken in conjunction with the accompanying drawings, illustrating by way of example the principles of the invention.

BRIEF DESCRIPTION OF THE DRAWINGS

Throughout the description similar reference numbers may be used to identify similar elements.

DETAILED DESCRIPTION OF THE INVENTION

Figure 1A:
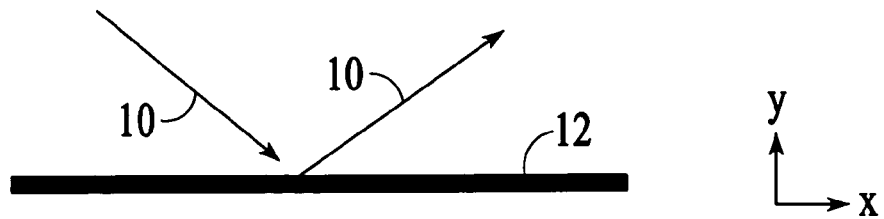
FIG. 1A illustrates light reflecting off the surface of a piece of paper that has a specular reflective characteristic.

Different printing media, particularly different types of paper, have different reflective characteristics. For example, glossy paper, such as photo-quality printing paper, has a smooth surface that tends to have a specular reflective characteristic. That is, the majority of light reflects off the surface of the paper at the same angle at which the light approaches the surface. FIG. 1A illustrates light 10 reflecting off the surface of a piece of paper 12 that has a specular reflective characteristic. In the example of FIG. 1A, light approaches the surface of the paper at approximately 60 degrees relative to the y-axis and the majority of light reflects off the surface of the paper at approximately 60 degrees.

Figure 1B:
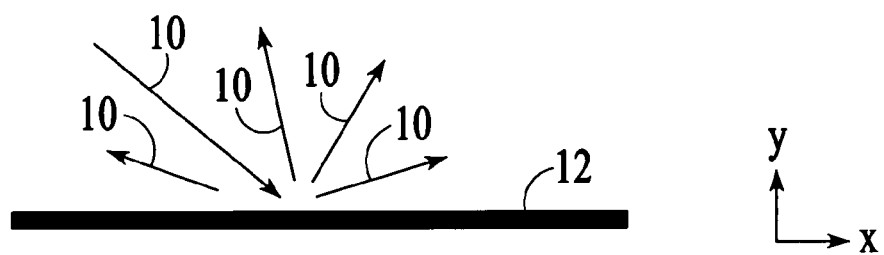
FIG. 1B illustrates light reflecting off the surface of a piece of paper that has a diffuse reflective characteristic.

Plain paper has a rougher, more fibrous, surface than glossy paper and tends to have a more diffuse reflective characteristic than glossy paper. That is, light reflects off the surface of plain paper with a broader angular distribution than that of glossy paper. FIG. 1B illustrates light 10 reflecting off the surface of a piece of paper 12 that has a diffuse reflective characteristic.

In accordance with the invention, a system for identifying a characteristic of a printing media includes a light source module that has a light emitting diode (LED) and an aspheric lens and a light detection module that has a photodetector and an aspheric lens. The light source module and light detection module are oriented with respect to a printing media such that the focusing points of the respective aspheric lenses are located at a common position on the printing media. The system differentiates between paper types by applying light to the surface of the paper and measuring the light that is reflected from the surface. Paper with a smooth surface, such as glossy photo-quality printing paper, tends to reflect a majority of light at the angle of incidence of the light. In contrast, paper with a rougher surface, such as plain paper, tends to diffuse light over a wide area. By strategically positioning the light source and light detection modules, it is possible to characterize the paper type based on the detected light.

Figure 2A:
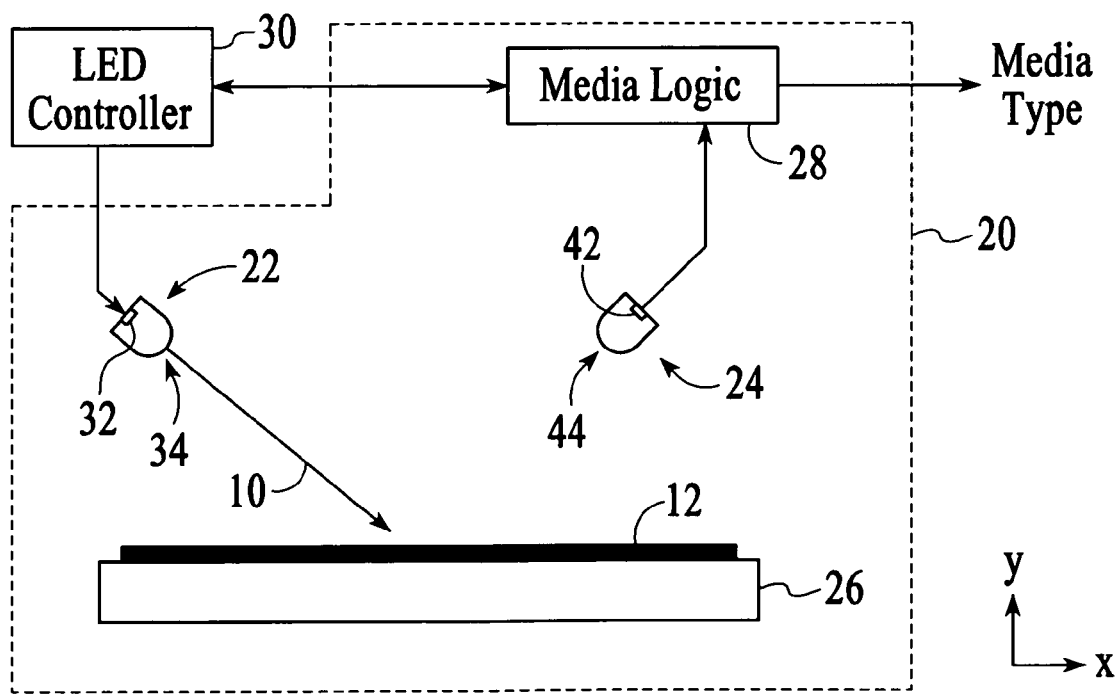
FIG. 2A depicts an embodiment of a system for identifying a characteristic of a printing media that utilizes aspheric lenses.
Figure 2B:
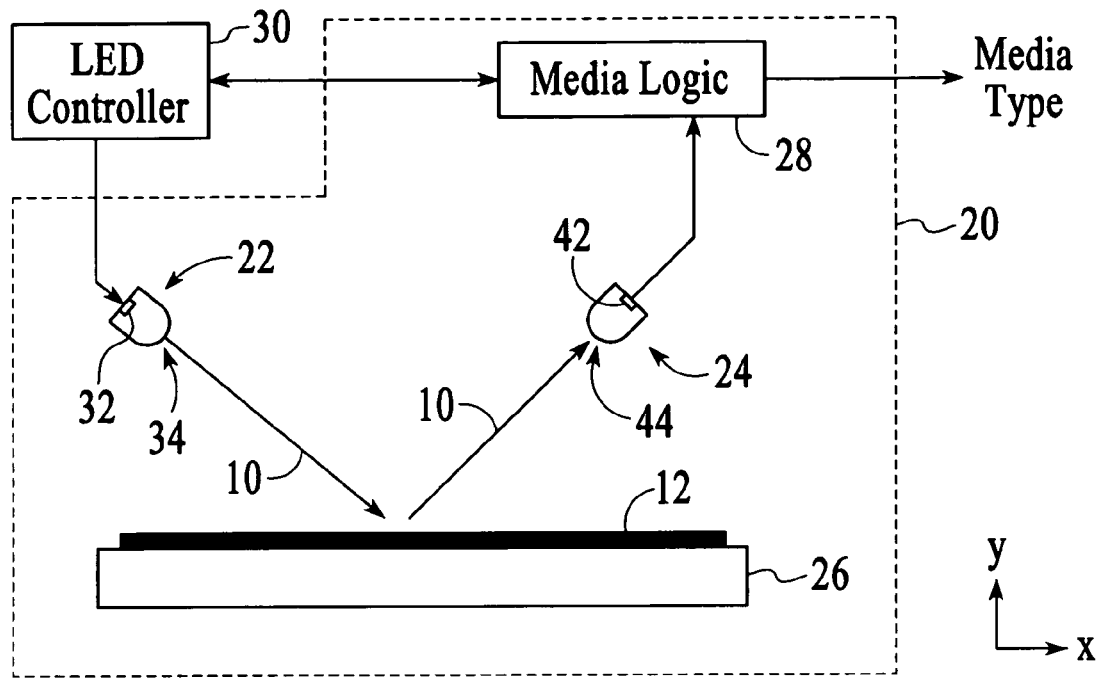
FIG. 2B illustrates the reflection of light in the system of FIG. 2A for the case in which the printing media has a predominantly specular reflective characteristic.
Figure 2C:
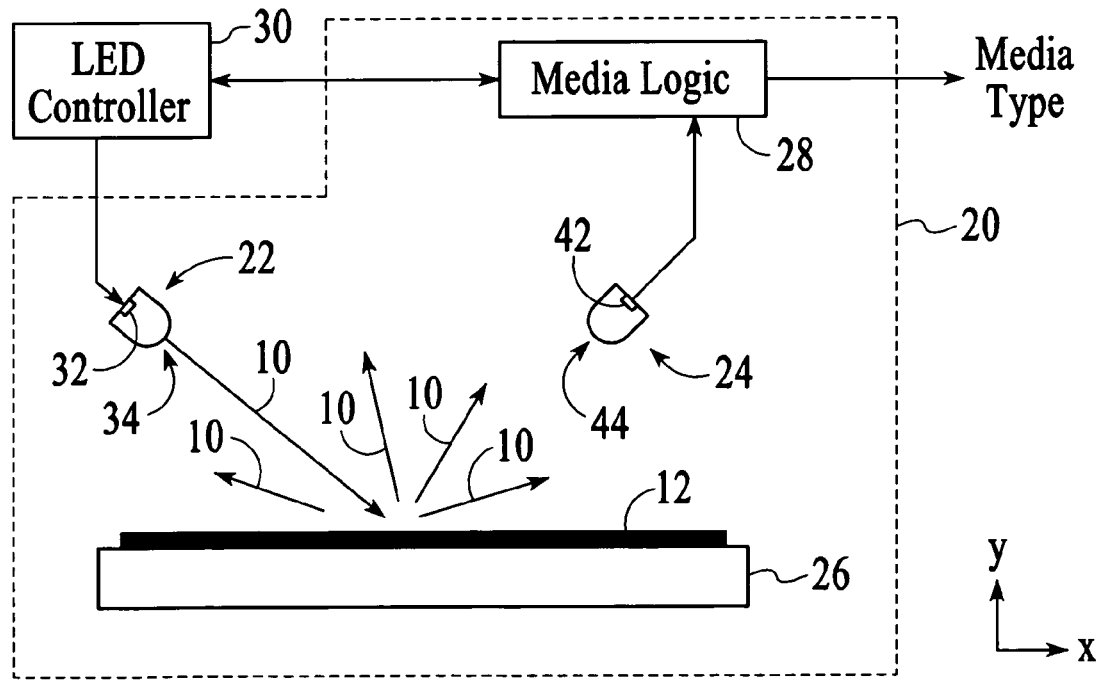
FIG. 2C illustrates the reflection of light in the system of FIG. 2A for the case in which the printing media has a predominantly diffuse reflective characteristic.

An embodiment of a system 20 for identifying a characteristic of a printing media 12 that utilizes aspheric lenses is depicted in FIGS. 2A-2C. The system depicted in FIGS. 2A-2C includes a light source module 22, a light detection module 24, a printing media handling structure 26, and media logic 28. The system is in signal communication with an LED controller 30.

The light source module 22 includes an LED 32 and an aspheric lens 34. Referring to FIG. 2A, the LED and aspheric lens are integrated into a single device. For example, the aspheric lens is molded onto the LED using well-known epoxy resin molding techniques. Alternatively, the aspheric lens may be molded glass that is attached to an LED package using a transparent adhesive. As is well-known in the field, the LED is typically embodied as an LED die that includes electrical connection points that can be connected to conductive wires, leads, traces, paths, etc. The LED die is then embedded into the aspheric lens via, for example, epoxy resin or glass molding.

The light detection module 24 includes a photodetector 42 and an aspheric lens 44. Referring again to FIG. 2A, the photodetector and aspheric lens are integrated into a single device. For example, the aspheric lens is molded onto the photodetector using well-known epoxy resin molding techniques. Alternatively, the aspheric lens may be molded glass that is attached to a photodetector package using a transparent adhesive. As is well-known in the field, the photodetector is typically embodied as a photodetector die that includes electrical connection points that can be connected to conductive wires, leads, traces, paths, etc. The photodetector die is then embedded into the aspheric lens via, for example, epoxy resin or glass molding.

Figure 3:
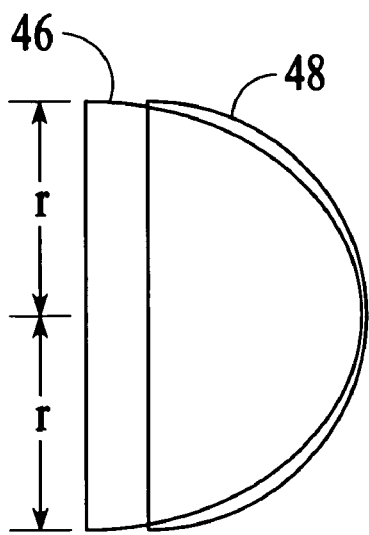
FIG. 3 depicts the geometry of an aspheric lens relative to the geometry of a spherical lens.

FIG. 3 depicts the geometry of an aspheric lens 46 relative to the geometry of a spherical lens 48. An aspheric lens can be characterized by a radius dimension, r, and a conic coefficient, k. In the embodiment of FIGS. 2A-2C, the aspheric lenses 34 and 44 have a radius of curvature of 1.176 mm and a conic coefficient, k, of −0.634406. Although an example of the radius and conic coefficient are provided, aspheric lenses with other characteristics (e.g., radius of curvature and conic constant) are possible.

Figure 4:
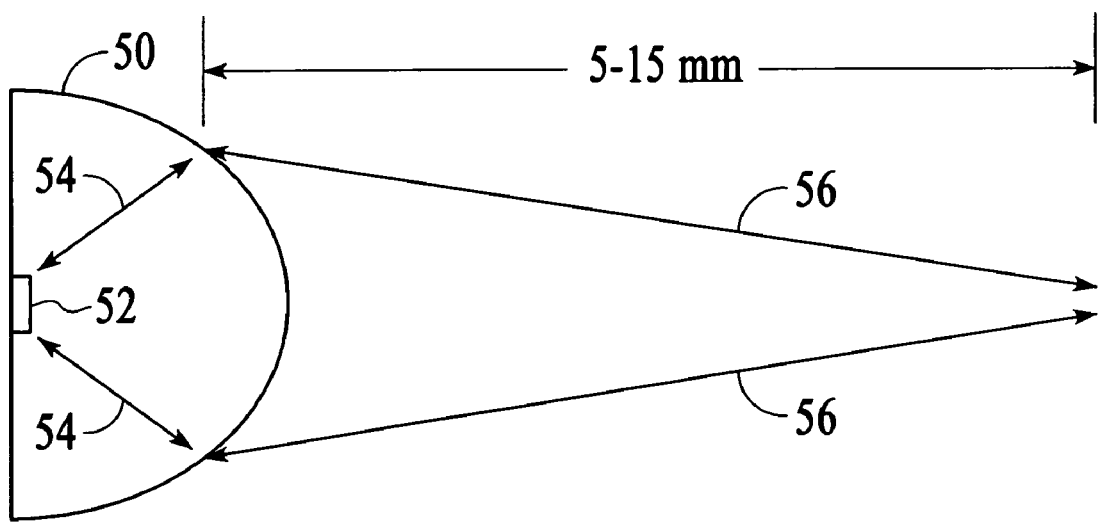
FIG. 4 depicts an embodiment of an aspheric lens integrated with either an LED or a photodetector.

Integrating the LED 32 and the photodetector 42 with aspheric lenses 34 and 44, respectively, enables light to be manipulated at the small geometries that are required in printing applications. FIG. 4 depicts an embodiment of an aspheric lens 50 integrated with either an LED or a photodetector 52. The aspheric lens has an internal focusing point as indicated by arrows 54 and an external focusing point as indicated by arrows 56. The internal focusing point is at the LED or photodetector and the external focusing point is approximately 5-15 mm from the apex of the lens' surface. In the embodiment of FIG. 2A, the aspheric lenses 34 and 44 of the light source and light detection modules 22 and 24 are configured to have a spot size of approximately 1-2 mm$^2$ at the desired separation distance from the printing media. In many printing applications the desired separation distance between the light source and light detection modules and the paper surface as measured along the y-axis is in the range of 2-5 mm. Although particular focusing distances and spot sizes are described, it should be understood that other focusing distances and spot sizes can be achieved by manipulating the characteristics (e.g., radius and conic constant) of the lens.

Referring back to FIG. 2A, the printing media handling structure 26 is a structure that holds the printing media 12 (e.g., paper) that is to be printed on by a printer. The printing media handling structure can be any structure as is known in the field for handling printing media. Examples of the printing media handling structure include alone or in combination, a paper tray, feed mechanisms, wheels, rollers, bars, tracks, conveyors, etc.

Figure 5:
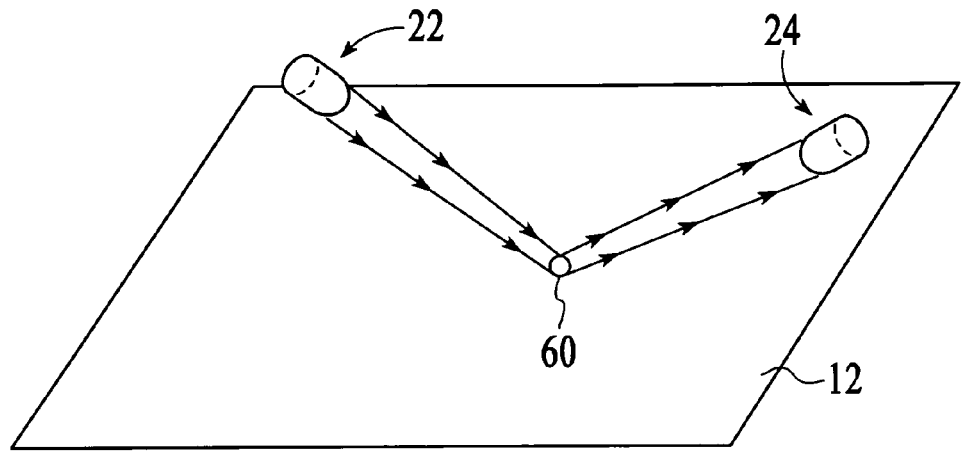
FIG. 5 is a perspective view of the external focusing points of the light source and light detection modules from FIG. 2A relative to a printing media.

In accordance with the invention, the light source module 22 and light detection module 24 are oriented relative to the printing media handling structure 26 such that the external focusing points of the respective aspheric lenses 34 and 44 are located at a common position on the printing media that is held by the printing media handling structure. FIG. 5 is a perspective view of the external focusing points 60 of the light source and light detection modules 22 and 24 from FIG. 2A relative to a printing media 12 that is positioned at the desired separation distance. As illustrated in FIG. 5, the light source and light detection modules are oriented such that the external focusing points of the two aspheric lenses are located at a common position on the printing media.

Referring back to FIG. 2A, in operation, the LED 32 of the light source module 22 is activated from the LED controller 30 to generate light 10. Light output from the light source module is focused by its aspheric lens 34. The focused light is incident on the printing media 12 and reflects off the surface of the printing media in a manner that is dictated by the media type. Light that reflects off the surface of the printing media at the same angle as the angle of approach is detected by the light detection module 24. Light that reflects off the surface of the printing media at other angles is not detected by the light detection module.

The photodetector 42 of the light detection module 24 generates an output signal that is indicative of the intensity of the detected light. The magnitude of the photodetector output signal (e.g., in terms of current or voltage) depends on the reflective characteristic of the printing media 12. If the printing media has a predominantly specular reflective characteristic, then the output of the photodetector will be relatively high because, as illustrated in FIG. 2B, a large portion of the incident light is reflected towards the light detection module. On the other hand, if the printing media has a predominantly diffuse reflective characteristic, then the output of the photodetector will be relatively low because, as illustrated in FIG. 2C, the incident light is scattered in a broad range of directions. The scattering of light reduces the amount of reflected light that reaches the light detection module.

The media logic 28 is in signal communication with the light detection module 24. The media logic receives the output signal from the light detection module and translates the output signal into an indication of a printing media type. For example, the media logic outputs a signal that indicates whether the printing media 12 is plain paper or glossy paper. In an embodiment, the media logic includes a signal threshold that is related to the printing media type such that an optical output above the signal threshold indicates glossy paper and an output signal below the signal threshold indicates plain paper.

Although one exemplary operation of the media logic 28 is described above, the media logic can be configured to perform other operations related to identifying a characteristic of a printing media. Additionally, the media logic may communicate with the LED controller 30 to coordinate operations.

Figure 6:
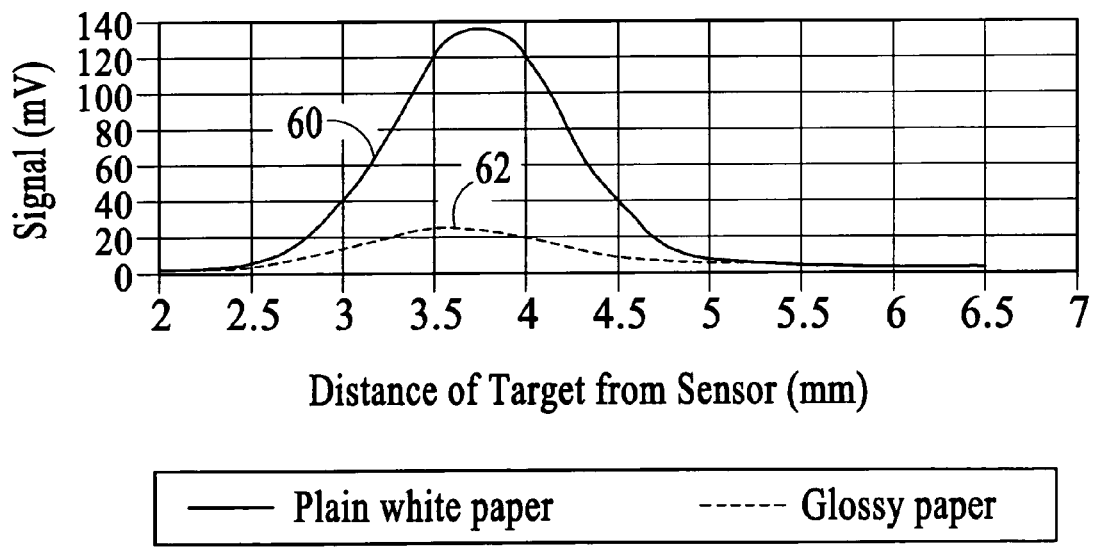
FIG. 6 is a graph of photodetector response vs. separation distance for plain paper and glossy paper.

A system in accordance with the invention was tested using light source and light detection modules with aspheric lenses configured as described above. The light source module was configured to provide light at an angle of approach of approximately 60 degrees relative to the y-axis and the light detection module was configured to receive light at the same angle. The light source and light detection modules were also strategically positioned such that the external focusing points of the respective aspheric lenses were located at a common position on the paper. During testing, the same intensity of input light was applied to plain white paper and then to photo-quality glossy paper. The distance along the y-axis between the light source and light detection modules and the paper was also varied over a range of approximately 2-6.5 mm for both types of paper. The responses 60 and 62 are summarized in the graph of FIG. 6. As depicted in the graph of FIG. 6, maximum response for both types of paper occurred at a separation distance in the range of approximately 2.75-4.5 mm. Further, the largest response ratio between the two different paper types occurred at a separation distance of approximately 3.5-4 mm. Looking, for example, at a separation distance of approximately 3.75 mm, the output signals from the photodetector related to plain and glossy paper were approximately:

25 mV for plain paper; and
130 mV for glossy paper.

These results give a plain paper-to-glossy paper response ratio of approximately 1:5.2. Because in this case the response ratio between plain paper and glossy paper is so large, a signal that indicates plain paper can easily be distinguished from a signal that indicates glossy paper, which in turn leads to reliable paper type determinations. A higher ratio may be desirable depending on the media type.

Figure 7A:
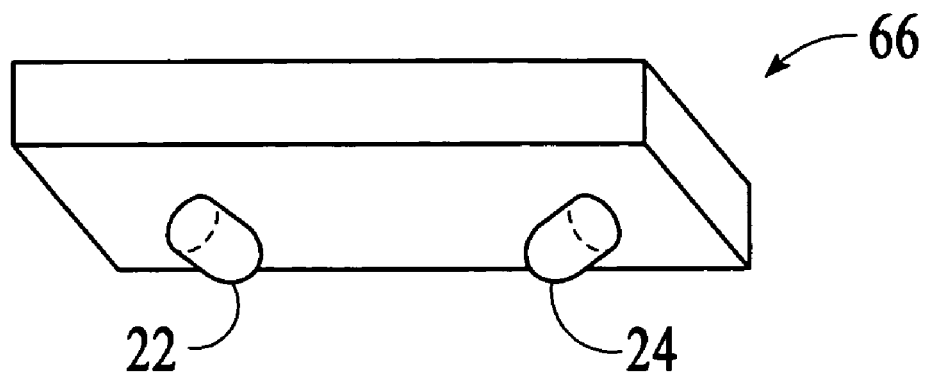
FIG. 7A depicts a perspective view of an embodiment of a system in which the light source module and light detection module are incorporated into a single module.
Figure 7B:
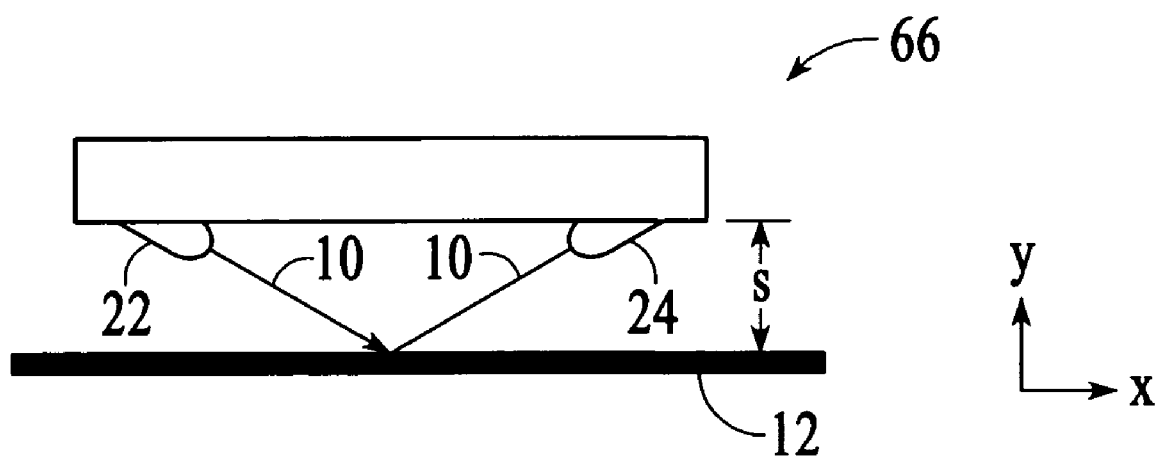
FIG. 7B depicts a side-view of the single module from FIG. 7A, which illustrates the propagation of light relative to the light source module, a paper surface, and the light detection module when the single module is separated from the paper by a separation distance, s.

In an embodiment, the light source module and light detection module are incorporated into a single module. FIG. 7A depicts a perspective view of an embodiment of a system in which the light source module 22 and light detection module 24 are incorporated into a single module 66. In this embodiment, the light source module and light detection module are pre-configured for a particular separation distance from the printing media. That is, the angles of the light source and light detection modules are pre-established such that light reflected from the surface of a piece of paper at the angle of incidence will be aligned with the light detection module. FIG. 7B depicts a side-view of the single module 66 from FIG. 7A, which illustrates the propagation of light relative to the light source module 22, the surface of a piece of paper 12, and the light detection module 24 when the single module is separated from the paper by a separation distance, s. In an embodiment, the separation distance, s, is in the range of 1-5 mm.

Figure 8:
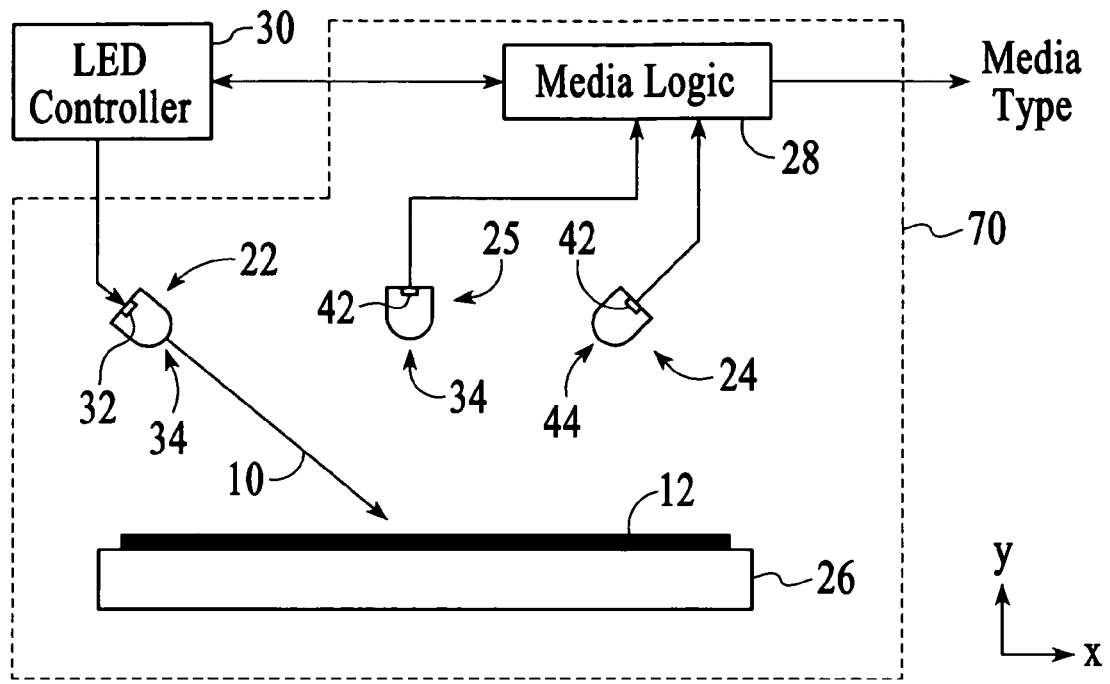
FIG. 8 depicts a system for identifying a characteristic of a printing media that simultaneously measures diffuse and specular reflections.

In an alternative embodiment, it is desirable to be able to measure diffuse reflections simultaneously with specular reflections. This can be achieved using two light detection modules, one that is positioned to detect specular reflections and one that is positioned to detect diffuse reflections. A system 70 for identifying a characteristic of a printing media that simultaneously measures diffuse and specular reflections is depicted in FIG. 8. The system of FIG. 8 includes a light source module 22, a diffuse light detection module 25, a specular light detection module 24, and a printing media handling structure 26. The system of FIG. 8 is similar to the system of FIG. 2 except that the system of FIG. 8 includes the diffuse light detection module, which is used to detect diffuse light reflections.

Figure 9:
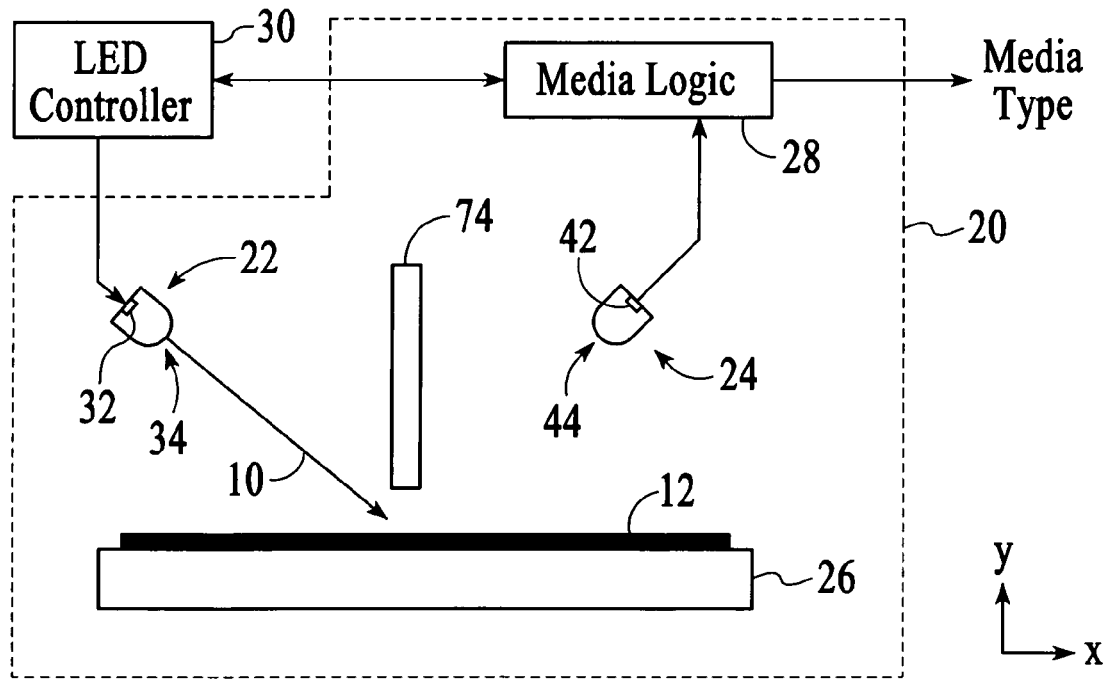
FIG. 9 depicts an embodiment of a system that includes a light shield between the light source module and light detection module.

In an embodiment, a light shield can be placed between the light source module and light detection module to improve the signal quality. An embodiment of a system that includes a light shield 74 between the light source module 22 and light detection module 24 is depicted in FIG. 9. The light shield can improve signal quality by blocking light from traveling directly from the light source module to the light detection module without reflecting off the printing media. The light shield can be any light blocking structure that can be located between the light source module and the light detection module.

Although the type of printing media 12 (e.g., paper type) is described as one characteristic of the printing media that is identified using the above-described system, the system can be used to identify other characteristics of the printing media. For example, the system may be used to identify the position of the printing media or to identify markings on the printing media.

Although the printing media is described primarily as paper, other types of printing media are possible. Further, although the printing media may have a predominantly specular or diffuse reflective characteristic, the reflective characteristic is not absolute. That is, printing media can have degrees of specular or diffuse reflectivity. In an embodiment, the media logic 28 can translate the photodetector output into more than two different paper types based on the degree of specular and/or diffuse reflection.

Although specific embodiments of the invention have been described and illustrated, the invention is not to be limited to the specific forms or arrangements of parts as described and illustrated herein. The invention is limited only by the claims.

What is claimed is:

1. A system for identifying a characteristic of a printing media for use with a printer, the system comprising:
   a light source module having a light emitting diode (LED) and an aspheric lens, the aspheric lens having an internal focusing point and an external focusing point, wherein the internal focusing point is at a location internal to the aspheric lens and the external focusing point is at a location external to the aspheric lens;
   a light detection module having a photodetector and an aspheric lens, the aspheric lens having an internal focusing point and an external focusing point and the aspheric lens being configured to focus received light onto the photodetector, wherein the internal focusing point is at a location internal to the aspheric lens and the external focusing point is at a location external to the aspheric lens;
   a printing media handling structure configured to bring the printing media in proximity to the light source module and the light detection module;
   wherein the light source module and the light detection module are oriented relative to the printing media handling structure at non-perpendicular angles relative to the printing media such that the external focusing points of the respective aspheric lenses are located at a common position on the printing media that is held by the printing media handling structure;
   wherein:
   the LED and the aspheric lens of the light source module are integrated into a single device;
   the photodetector and the aspheric lens of the light detection module are integrated into a single device; and
   the light source module and the light detection module are incorporated into a single module, wherein the light source module and the light detection module are pre-configured within the single module for a particular separation distance from the printing media, further comprising media logic configured to output an indication of a printing media characteristic in response to an output signal from the photodetector.

2. The system of claim 1 wherein the photodetector generates output signals at least a 1:5 ratio in response to plain paper and glossy paper, respectively, as the printing media.

3. The system of claim 1 wherein the aspheric lens of the light source module is molded onto the LED.

4. The system of claim 1 wherein the aspheric lens of the light source module is configured such that the external focusing point focuses light at a spot size of 1-2 mm$^2$ at a distance in the range of 5-15 mm.

5. The system of claim 1 wherein the aspheric lens of the light detection module is molded onto the photodetector.

6. The system of claim 1 wherein the aspheric lens of the light detection module is configured such that the external focusing point focuses light at a spot size of 1-2 mm$^2$ at a distance in the range of 5-15 mm.

7. The system of claim 1 further comprising a light shield oriented with respect to the light source module and the light detection module to block light from traveling directly from the light source module to the light detection module.

8. The system of claim 1 wherein the particular separation distance from the printing media is in the range of 1-5 mm.

9. A system for identifying a characteristic of a printing media for use with a printer, the system comprising:
 a light source module having an aspheric lens molded onto a light emitting diode (LED), the aspheric lens having an internal focusing point and an external focusing point, wherein the internal focusing point is at a location internal to the aspheric lens and the external focusing point is at a location external to the aspheric lens;
 a light detection module having an aspheric lens molded onto a photodetector, the aspheric lens having an internal focusing point and an external focusing point and the aspheric lens being configured to focus received light onto the photodetector, wherein the internal focusing point is at a location internal to the aspheric lens and the external focusing point is at a location external to the aspheric lens;
 a printing media handling structure configured to bring the printing media in proximity to the light source module and the light detection module;
 wherein the light source module and the light detection module are oriented relative to the printing media handling structure at non-perpendicular angles relative to the printing media such that the external focusing points of the respective aspheric lenses are located at a common position on the printing media that is held by the printing media handling structure; and
 media logic configured to output an indication of a printing media characteristic in response to an output signal from the photodetector;
 wherein the light source module and the light detection module are incorporated into a single module and wherein the light source module and the light detection module are pre-configured within the single module for a separation distance from the printing media in the range of 1-5 mm.

10. The system of claim 9 wherein the photodetector generates output signals at least a 1:5 ratio in response to plain paper and glossy paper, respectively, as the printing media.

11. The system of claim 10 wherein the aspheric lens of the light source module is configured such that the external focusing point focuses light at a spot size of 1-2 mm$^2$ at a distance in the range of 5-15 mm.

12. The system of claim 9 wherein the aspheric lens of the light detection module is configured such that the external focusing point focuses light at a spot size of 1-2 mm$^2$ at a distance in the range of 5-15 mm.

13. The system of claim 9 wherein the aspheric lenses of the light source module and the light detection module have a radius of curvature of approximately 1.176 mm and a conic coefficient, k, of approximately −0.634406.

14. The system of claim 9 wherein the light source module is configured to provide light at an angle of approach to the printing media of approximately 60 degrees relative to an axis that is perpendicular to the printing media and wherein the light detection module is configured to receive light at an angle of approximately 60 degrees relative to the axis that is perpendicular to the printing media.

15. A system for identifying a paper type for use with a printer, the system comprising:
 a single module comprising:
  a light source module having an aspheric lens molded onto a light emitting diode (LED), the aspheric lens having an internal focusing point and an external focusing point, wherein the internal focusing point is at a location internal to the aspheric lens and the external focusing point is at a location external to the aspheric lens;
  a light detection module having an aspheric lens molded onto a photodetector, the aspheric lens having an internal focusing point and an external focusing point and the aspheric lens being configured to focus received light onto the photodetector, wherein the internal focusing point is at a location internal to the aspheric lens and the external focusing point is at a location external to the aspheric lens;
 a paper handling structure configured to bring a piece of paper in proximity to the light source module and the light detection module;
 wherein the light source module and the light detection module are oriented relative to the paper handling structure at non-perpendicular angles relative to the printing media such that the external focusing points of the respective aspheric lenses are located at a common position on the piece of paper that is held by the paper handling structure and wherein the light source module and the light detection module are pre-configured within the single module for a separation distance from the piece of paper in the range of 1-5 mm; and
 media logic configured to output an indication of the type of paper that is held by the printing media handling structure in response to an output signal from the photodetector.

16. The system of claim 15 wherein the photodetector generates output signals at least a 1:5 ratio in response to plain paper and glossy paper, respectively, as the printing media.

17. The system of claim 16 wherein the media logic is configured to indicate whether the paper is plain paper or glossy paper.

18. The system of claim 17 wherein the aspheric lens of the light source module is configured such that the external focusing point focuses light at a spot size of 1-2 mm$^2$ at a distance in the range of 5-15 mm and the aspheric lens of the light detection module is configured such that the external focusing point focuses light at a spot size of 1-2 mm$^2$ at a distance in the range of 5-15 mm.

19. The system of claim 15 wherein the single module is directly adjacent to the paper handling structure such that light travels from the light source module to the piece of paper and from the piece of paper to the light detection module without passing through another optical element.

* * * * *